(12) United States Patent
Broecker et al.

(10) Patent No.: US 6,369,277 B1
(45) Date of Patent: Apr. 9, 2002

(54) SELECTIVE LIQUID-PHASE HYDROGENATION OF α,β-UNSATURATED CARBONYL COMPOUNDS

(75) Inventors: Franz Josef Broecker, Ludwigshafen; Gerd Kaibel, Lampertheim; Werner Aquila, Mannheim; Hartwig Fuchs, Ludwigshafen; Guenter Wegner, Roemerberg; Manfred Stroezel, Ilvesheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/645,583

(22) Filed: Aug. 25, 2000

Related U.S. Application Data

(63) Continuation-in-part of application No. 09/275,867, filed on Mar. 25, 1999, now Pat. No. 6,150,564.

(30) Foreign Application Priority Data

Apr. 2, 1998 (DE) .......................................... 198 14 879

(51) Int. Cl.[7] .............................................. C07C 45/62
(52) U.S. Cl. ........................ 568/462; 568/396; 568/395; 568/458; 568/459
(58) Field of Search ................................ 568/396, 395, 568/462, 458, 459

(56) References Cited

U.S. PATENT DOCUMENTS 4,320,228 A 3/1982 Horner
4,847,016 A 7/1989 Goebel

FOREIGN PATENT DOCUMENTS

| | | |
|---|---|---|
| CA | 2201014 | 9/1997 |
| DE | 2 114 211 | 10/1971 |
| DE | 28 39 474 | 3/1980 |
| DE | 29 36 362 | 4/1981 |
| DE | 226 872 | 9/1985 |
| DE | 195 30 329 | 2/1997 |
| DE | 196 41 707 | 4/1998 |
| EP | 0 024 651 | 3/1981 |
| EP | 0 798 039 | 10/1997 |
| FR | 2 247 445 | 5/1975 |

*Primary Examiner*—Sreeni Padmanabhan
(74) *Attorney, Agent, or Firm*—Oblon, Spivak, McClelland, Maier & Neustadt, P.C.

(57) ABSTRACT

An α,β-unsaturated carbonyl compound of formula (I)

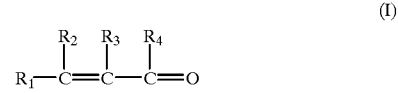

(I)

where $R_1$ is saturated $C_{1-40}$-hydrocarbyl or a substituted or unsubstituted aromatic radical containing moiety, and $R_2$, $R_3$ and $R_4$, independently of one another, are hydrogen or a $C_1$- to $C_4$-alkyl group, is selectively hydrogenated in the liquid phase to a saturated carbonyl compound of formula (II)

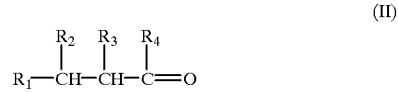

(II)

with hydrogen in the presence of a pulverulent palladium and/or rhodium catalyst and in the presence of an organic base, by conducting the hydrogenation in a packed bubble column reactor in which product is recycled and hydrogen gas is recirculated.

28 Claims, 2 Drawing Sheets

SELECTIVE LIQUID-PHASE HYDROGENATION OF α,β-UNSATURATED CARBONYL COMPOUNDS

CROSS-REFERENCE TO RELATED APPLICATIONS

The present application is a continuation-in-part of application U.S. Ser. No. 09/275,867 filed Mar. 25, 1999, now U.S. Pat. No. 6,150,564.

BACKGROUND OF THE INVENTION

1. Field of the Invention

The present invention relates to a process for the selective liquid-phase hydrogenation of α,β-unsaturated carbonyl compounds.

2. Description of the Background

Processes for the selective hydrogenation of α,β-unsaturated carbonyl compounds using hydrogen in the liquid phase are described, for example, in DE-A-21 14 211 and DE-A-28 39 474. Both processes operate batchwise in the presence of a palladium catalyst and a base, the process of DE-A-28 39 474 using from 15 to 50% by weight of a tertiary amine, based on the starting material, exhibiting improved selectivity and space-time yield of the hydrogenation reaction. However, even this improvement does not give satisfactory reaction times. Although the reaction times can be shortened by using larger amounts of the palladium catalyst, this is, however, uneconomical because of high catalyst costs, and in addition larger amounts of catalyst are disadvantageous in view of the problems of handling solids. Neither is successful regeneration of the deactivated catalyst generally possible.

SUMMARY OF THE INVENTION

Accordingly, one object of the present invention is to provide a method of hydrogenating α,β-unsaturated carbonyl compounds of the formula (I) to the corresponding α,β-unsaturated carbonyl compounds of the formula (II) in a more economical manner, while improving the space-time yield and reducing the investment costs.

Another object of the present invention is to provide a method of more economically hydrogenating citral to citronellal.

Briefly, these objects and other objects of the present invention as hereinafter will become more readily apparent can be attained by a process for the selective liquid-phase hydrogenation of α,β-unsaturated carbonyl compounds of the formula (I)

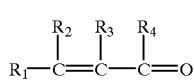

(I)

where $R_1$ is hydrogen or an organic radical, and $R_2$, $R_3$ and $R_4$, independently of one another, are hydrogen or a $C_1$- to $C_4$-alkyl group, to saturated carbonyl compounds of the formula (II)

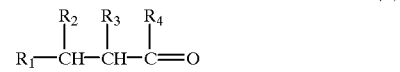

(II)

with hydrogen in the presence of a pulverulent palladium and/or rhodium catalyst and in the presence of an organic base, which comprises conducting the hydrogenation in a packed bubble column reactor in which the product is recycled and the hydrogen gas is recirculated.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
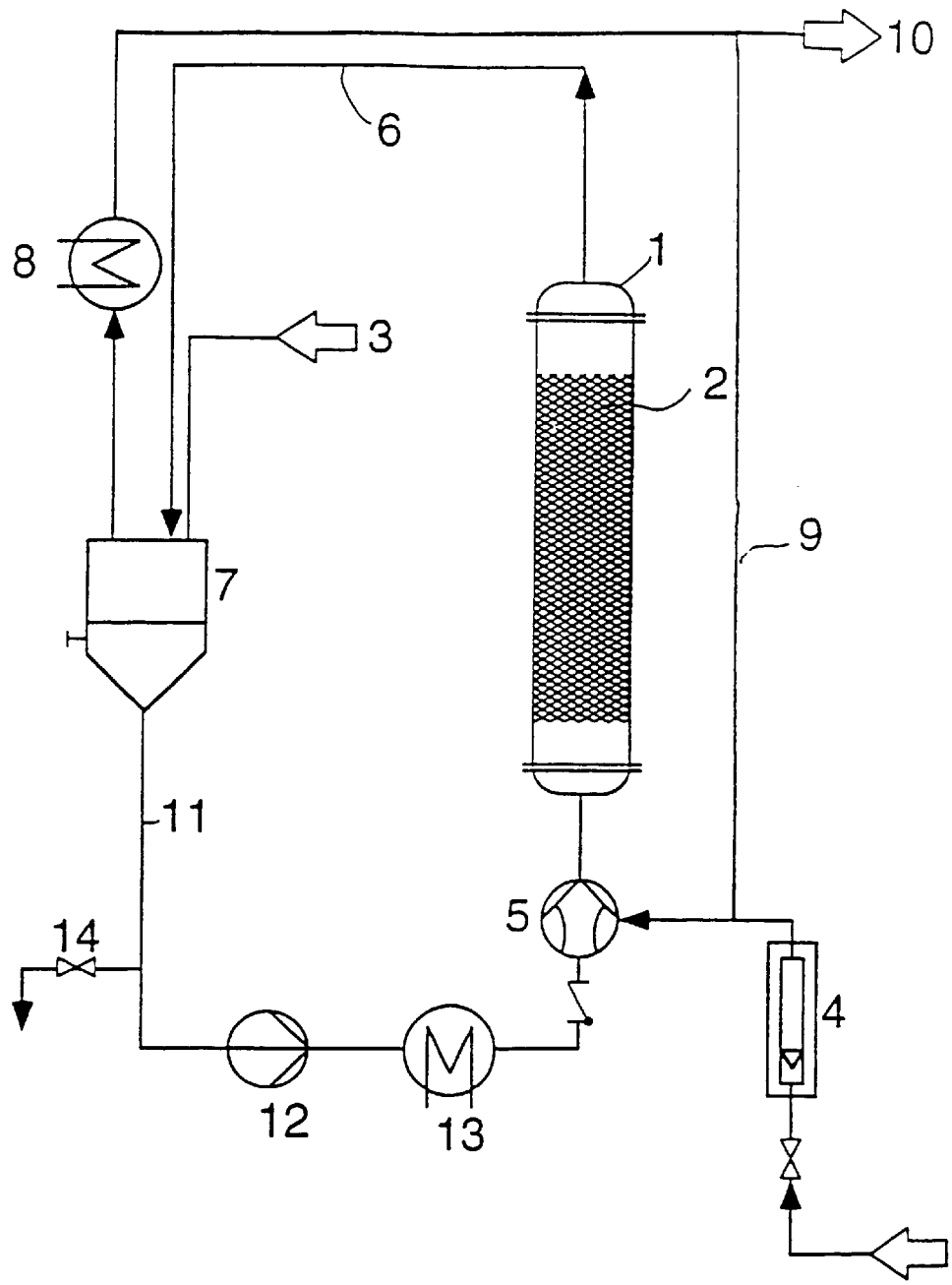
FIG. 1 shows a diagrammatic representation of a plant for a batch process in accordance with the invention.

In formula (1) above, substituent $R_1$, as an organic radical, preferably, is saturated $C_{1-40}$ hydrocarbyl, particularly saturated $C_{1-10}$ hydrocarbyl, olefinically unsaturated hydrocarbyl or substituted or unsubstituted aromatic such as p-tert-butylphenyl.

It has been found that the rate-determining step in the process as a whole, namely diffusion of the gaseous hydrogen to the catalyst surface, can be accelerated by conducting the process in a packed bubble column reactor with product recycling and circulating hydrogen gas. As the reaction proceeds, the hydrogen concentration in the liquid in the vicinity of the catalyst surface drops. This low-hydrogen film at the catalyst surface can then, through the novel use of a packed bubble column reactor with product recycling and circulating hydrogen gas, be swirled around in such a way that exchange with hydrogen-saturated liquid from the outside becomes possible. A crucial role is played here by the increased relative motion of the catalyst particles with respect to the liquid phase and the hydrogen gas bubbles, which is caused by the catalyst particles being slowed down and briefly held at the packing channel walls. The improved hydrodynamics mean that the catalyst is utilized particularly well.

The present process may in principle be used for all α,β-unsaturated carbonyl compounds of the formula (I), the shortened reaction time improving the selectivity with respect to hydrogenation of the double bond, i.e. the individual reaction with the larger rate constant. In a preferred embodiment, the starting material citral is converted to citronellal.

The pulverulent palladium and/or rhodium catalyst can be used in the form of a supported or unsupported catalyst, preferred support materials being carbon, zirconium dioxide or titanium dioxide. It is particularly advantageous to use catalyst supports having a mean particle size of from 0.1 to 300 μm, preferably from 0.5 to 100 μm. These catalyst particles, with their high surface area per unit volume, result in good space-time yields since they are able, when flowing through the openings and channels in the bubble column reactor packing, to execute relative movements with respect to the liquid phase and the hydrogen gas bubbles.

The hydrogenation is conducted in a packed bubble column reactor. Particularly suitable packing has openings or channels whose hydraulic diameter is from 0.5 to 20 mm, preferably from 1 to 10 mm, particularly preferably from 1 to 3 mm. The hydraulic diameter is defined as the quotient of the quadruple opening cross section and its circumference. The suspended catalyst particles are slowed down in the packing openings or channels by collisions with the channel walls and by brief holding. It has been observed that, for hydraulic diameters in the above range, on average a proportion of about 15 to 16% by weight of the catalyst is held on the packing walls at any one time.

This effect can be further improved by increasing the surface roughness of the walls. Preferred wall materials have surface roughness values in the range from 0.1 to 10 times, preferably from 0.5 to 5 times, the mean particle size of the suspended catalyst particles. Particularly suitable wall materials are metallic and have a surface with a mean roughness $R_a$, measured in accordance with EN ISO 4287, of from 0.001 to 0.01 mm.

Suitable packing materials are metallic materials, plastics, ceramics and/or inorganic fibers, in particular carbon or asbestos substitutes.

The packing can be in the form of foils, gauzes or meshes, as are already known in principle, i.e. with respect to their geometrical shape, from distillation or extraction technology. Packing elements of this type, which offer the advantage of low pressure loss, are, for example, wire mesh packing of the Montz A3 and Sulzer BX, DX and EX type. For the purposes of the present invention, however, the packing basically has a hydraulic diameter which is essentially smaller, generally by a factor of from 2 to 10, than comparable internals in the area of distillation or extraction technology. Wire mesh packing is particularly advantageous. For the purposes of the present invention, however, mesh packing can also be replaced by packing made from other woven, knitted or felted, liquid-permeable materials. In other suitable packing, flat metal sheets, preferably without perforations or other relatively large openings, are used, for example as in the Montz B1 or Sulzer Mellapak types. Also advantageous is packing made from expanded metal, for example packing of the Montz BSH type. Here too, openings, for example perforations, must be kept appropriately small. The crucial factor for the suitability of packing for the purposes of the present invention is not its geometry, but the opening sizes or channel widths formed in the packing for flow passage.

In a preferred process, the liquid phase is pumped through the packed bubble column reactor at a superficial velocity of from 100 to 500 m$^3$/m$^2$.h, preferably from 150 to 300 m$^3$/m$^2$.h.

The circulating hydrogen gas is fed to the liquid phase containing suspended pulverulent catalyst at a preferred superficial velocity of 0.5 to 15 cm/s, preferably from 2.5 to 10 cm/s. The circulating hydrogen gas is preferably introduced via a gas jet compressor, which effects intensive mixing with the liquid phase and the catalyst suspended therein.

The hydrogenation is preferably conducted at a hydrogen partial pressure of from 1 to 200 bar, preferably from 1 to 100 bar, particularly preferably from 1 to 10 bar.

Preferred reaction temperatures are from 25 to 150° C., particularly from 50 to 100° C.

The process can be conducted either batchwise or continuously. The continuous a procedure is particularly advantageous. In this, the spent catalyst can be separated off by the particularly favorable method of cross-flow filtration.

The liquid phase containing suspended catalyst and the hydrogen are preferably circulated cocurrently. It is particularly advantageous to feed the starting materials to a vertical bubble column reactor from below.

FIG. 1 shows, by way of example, a diagrammatic representation of a plant having a bubble column reactor 1 operated batchwise, which is filled with packing 2 whose geometry is comparable to that of the Montz-Pak type A3-1200 distillation packing.

In order to carry out the hydrogenation, the storage tank 7 is first filled with starting material, amine and suspension catalyst via the fill line 3. By means of the circulation pump 12, the reaction mixture is pumped via the preheater 13 and the gas jet compressor 5 into the reactor and from the latter back via the circulation line 6 into the storage tank 7. Here, the unreacted hydrogen is separated off and fed back via the circulating gas line 9 to the mixing nozzle 5 and thus to the reactor inlet and mixed intimately with the circulating suspension. The hydrogen consumed is replaced continuously via the fresh hydrogen line 4. A certain amount of offgas can be passed through the offgas line 10 in order to prevent accumulation of inert gases.

When the hydrogenation is complete, the suspension is discharged via the withdrawal line 14.

The high space-time yield in this procedure is achieved by circulating the suspension at a rate of from 100 to 500 m$^3$/m$^2$.h and preferably from 150 to 300 m$^{3/m2}$.h, based on the free reactor cross section, and distributing the hydrogen optimally in the suspension via the gas jet compressor 5.

This procedure generates increased turbulence in the gas-containing suspension within in the packing. The catalyst particles execute an increased relative motion with respect to the liquid because, in the narrow openings and channels of the packing, they experience a deceleration with respect to the liquid surrounding them and the rising gas bubbles.

Figure 2:
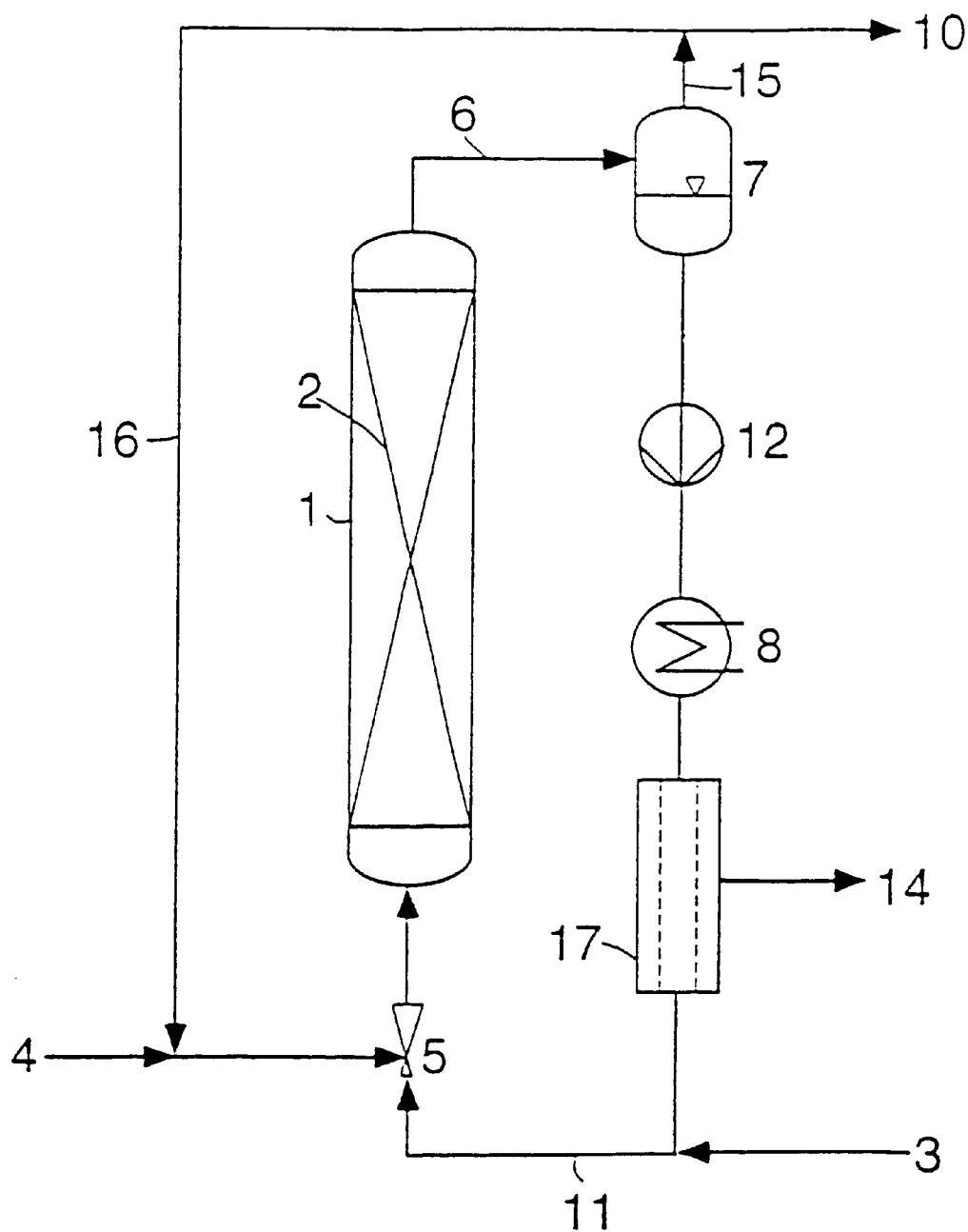
FIG. 2 shows a diagrammatic representation of a plant for the particularly preferred continuous implementation of the process of the invention.

FIG. 2 shows a particularly advantageous continuous procedure. The reactor 1 is filled with packing 2 and provided with a liquid and gas circulation. Firstly, the entire circuit is filled with suspension, advantageously prehydrogenated product and suspension catalyst, via the feed line 3. By means of the circulation pump 12, the suspension is fed via the preheater 8 and the cross-flow filtration unit 17 to the mixing nozzle 5. The mixing nozzle is a gas jet compressor which sucks the hydrogen in via the circulating gas lines 15 and 16 and mixes it vigorously with the suspension. If the circulation is implemented in this way, the starting material to be hydrogenated is introduced via the feed line 3. The requisite hydrogen is fed in continuously via the H$_2$ line 4 by means of a pressure maintenance system.

Suspension and hydrogenation water are mixed intimately in reactor 1 in the openings and channels of the packing, resulting in correspondingly good hydrogenation. The reactor products enter the separator 7 via line 6. In the separator, the gas phase is separated off and fed back to the reactor inlet via the circulating gas lines 15 and 16. A certain amount of offgas can be removed via the offgas line 10. This prevents accumulation of inert gases in the hydrogen.

The suspended catalyst remains in the reactor system by being retained by the cross-flow filter 17. The catalyst-free product is discharged as permeate via 14.

For a production plant with packed bubble column reactor as shown in FIG. 2, the investment costs are only about ¼ of the costs for a conventional stirred reactor plant of the same space-time yield.

Having generally described this invention, a further understanding can be obtained by reference to certain specific examples which are provided herein for purposes of illustration only and are not intended to be limiting unless otherwise specified.

EXAMPLES

Example 1

The reactor of an apparatus which, in accordance with FIG. 1, is suitable for batch hydrogenation, was charged with five monoliths having a diameter of 27 mm and a height of 5 cm and consisting of $V_2A$ mesh, material No. 4301, having a cross-channel structure (module 1.0 mm). The plain-woven wire mesh has a mesh width of 0.18 mm and a wire diameter of 0.105 mm. The apparatus was charged via a fill hopper with 550 ml of citral solution consisting of 70% by weight of citral, 27% by weight of methanol and 3% by weight of trimethylamine, and 5 g of pulverulent palladium/carbon catalyst (5% by weight of Pd). The latter had a particle size distribution of between 0.001 and 0.2 mm with a 50% value of 0.012 mm, measured using a Cilas laser spectrometer by the sedimentation method in accordance with DIN standard 66111. After injection of hydrogen to 8 bar via the $H_2$ feed line 4, the circulation pump 12 was switched on and a flow rate of 200 $m^3/m^2 \cdot h$, based on the free reactor cross section, was established. The nozzle of the gas jet compressor then sucked hydrogen in via the circulating gas line 9 and aerated the reactor at a gas velocity of 5.5 cm/s. By means of the preheater 13, the reactor inlet temperature was raised to 70° C. During the hydrogenation, samples were taken from the circulation at certain time intervals via the valve 14 and analyzed by gas 5 chromatography.

After 2.75 h, a citral conversion of 99.5% and selectivity of 94% had been achieved. The space-time yield, based on the Pd/C catalyst, was 22.4 kg of citral/$kg_{cat} \cdot h$.

Comparative Example 1

6.91 of citral solution consisting of 70% by weight of citral, 27% by weight of methanol and 3% by weight of trimethylamine, and 55 g of pulverulent palladium/carbon catalyst (5% by weight of Pd) were introduced into a 10 liter stirred reactor with gas dispersion stirrer. The particle size of the catalyst corresponded to that in Example 1.

After hydrogen had been injected and the reactor had been heated to 70° C., the mixture was hydrogenated at 8 bar of $H_2$ with stirring at 800 revolutions per minute. The progress of the hydrogenation was analyzed by means of samples taken at certain time intervals and analyzed by gas chromatography. After 19 hours, the citral conversion was 99.7% and the product selectivity was 92.9%. The space-time s yield, based on the pulverulent Pd/C catalyst, was 3.68 $kg_{citral}/kg_{cat}*h$.

The disclosure of German priority application Serial Number 19814879.8 filed Apr. 2, 1998 is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended tom be secured by letters patent is:

1. A process of selectively hydrogenating an α,β-unsaturated carbonyl compound of the formula (I)

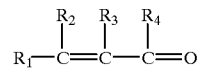

(I)

where $R_1$ is saturated $C_{1-40}$-hydrocarbyl, unsaturated hydrocarbyl or a substituted or unsubstituted aromatic radical containing moiety, and $R_2$, $R_3$ and $R_4$, independently of one another, are hydrogen or a $C_1$- to $C_4$-alkyl group, in the liquid phase to a saturated carbonyl compound of the formula (II)

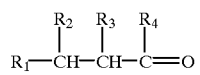

(II)

with hydrogen in the presence of a pulverulent palladium and/or rhodium catalyst and in the presence of an organic base, which comprises:
 conducting the hydrogenation in a packed bubble column reactor in which product is recycled and hydrogen gas is recirculated.

2. The process as claimed in claim 1, wherein $R_1$ is p-tert-butylphenyl.

3. The process as claimed in claim 1, wherein the packing in the bubble column reactor has openings and channels whose hydraulic diameter ranges from 0.5 to 20 mm.

4. The process as claimed in claim 3, wherein the hydraulic diameter ranges from 1 to 10 mm.

5. The process as claimed in claim 4, wherein the hydraulic diameter ranges from 1 to 3 mm.

6. The process as claimed in claim 1, wherein the walls of the openings or channels of the packing in the bubble column reactor have surface roughness values in the range from 0.1 to 10 times the mean particle size of the pulverulent catalyst particles.

7. The process as claimed in claim 6, wherein said surface roughness values range from 0.5 to 5 times, the mean particle size of the pulverulent catalyst particles.

8. The process as claimed in claim 1, wherein the walls of the openings or channels of the packing in the bubble column reactor are metallic and have a mean roughness $R_a$, measured in accordance with EN ISO 4287, of from 0.001 to 0.01 mm.

9. The process as claimed in claim 1, wherein the packing in the bubble column reactor is made of metallic materials, plastics, ceramics and/or inorganic fibers.

10. The process as claimed in claim 9, wherein the fibers are carbon or asbestos fibers.

11. The process as claimed in claim 9, wherein the packing is a foil, gauze or mesh.

12. The process as claimed in claim 1, wherein the palladium and/or rhodium catalyst is supported on a support of carbon, zirconium dioxide or titanium dioxide, having a mean particle size ranging from 0.1 to 300 µm.

13. The process as claimed in claim 12, wherein said mean particle size ranges from 0.5 to 100 µm.

14. The process as claimed in claim 12, wherein the supported catalyst contains from 0.01 to 10% by weight of palladium and/or rhodium.

15. The process as claimed in claim 14, wherein the supported catalyst contains from 0.2 to 5% by weight of palladium and/or rhodium.

16. The process as claimed in claim 14, wherein the supported catalyst contains from 0.5 to 1% by weight of palladium and/or rhodium.

17. The process as claimed in claim 1, wherein the liquid phase is circulated at a superficial velocity ranging from 100 to 500 m$^3$/m$^2$.h.

18. The process as claimed in claim 17, wherein said superficial velocity ranges from 150 to 300 m$^3$/m$^2$.h.

19. The process as claimed in claim 1, wherein the hydrogen is fed in at a superficial velocity of from 0.5 to 15 cm/s.

20. The process as claimed in claim 19, wherein the hydrogen is fed in at a superficial velocity ranging from 2.5 to 10 cm/s by means of a gas jet compressor.

21. The process as claimed in claim 1, wherein the hydrogenation is conducted at a hydrogen partial pressure ranging from 1 to 200 bar.

22. The process as claimed in claim 21, wherein said hydrogen partial pressure ranges from 1 to 100 bar.

23. The process as claimed in claim 22, wherein said hydrogen partial pressure ranges from 1 to 10 bar.

24. The process as claimed in claim 1, wherein the hydrogenation is conducted at a temperature ranging from 25 to 150° C.

25. The process as claimed in claim 24, wherein the temperature ranges from 50 to 100° C.

26. The process as claimed in claim 1, which is conducted continuously.

27. The process as claimed in claim 1, wherein the liquid phase and the hydrogen are conveyed cocurrently, from bottom to top through a vertical bubble column reactor.

28. The process as claimed in claim 1, wherein the α,β-unsaturated carbonyl compound of the formula (I) is citral.

* * * * *

UNITED STATES PATENT AND TRADEMARK OFFICE
CERTIFICATE OF CORRECTION

PATENT NO. : 6,369,277 B1
DATED : April 9, 2002
INVENTOR(S) : Franz J. Broecker et al.

It is certified that error appears in the above-identified patent and that said Letters Patent is hereby corrected as shown below:

Column 4,
Line 35, "within in the packing" should read -- within the packing --.

Signed and Sealed this

Sixteenth Day of July, 2002

*Attest:*

*Attesting Officer*

JAMES E. ROGAN
*Director of the United States Patent and Trademark Office*